United States Patent [19]

Kerrigan

[11] Plant 4,749

[45] Jun. 30, 1981

[54] AZALEA PLANT

[76] Inventor: Howard Kerrigan, 24249 Second St., Hayward, Calif. 94541

[21] Appl. No.: 120,721

[22] Filed: Feb. 11, 1980

[51] Int. Cl.[3] ..... A01H 5/00

[52] U.S. Cl. ..... Plt./57

[58] Field of Search ..... Plt./57

*Primary Examiner*—Robert E. Bagwill

*Attorney, Agent, or Firm*—James R. Cypher

[57] ABSTRACT

This invention relates to a new and distinct variety of Azalea plant named "Super Red" which is a hybrid cultivar of pollen parent U.S. Plant Pat. No. 2,939 named "Ripples" and undisseminated seedling 57 D-2.

"Super Red" is distinctly different than either of its parents or any other azalea of which I am aware, in that it has a very large, very double, clear red flower and an unusually rapid and strong growth habit.

2 Drawing Figures

BACKGROUND OF THE INVENTION

The present new and distinct variety was originated by me in 1974 as a result of a breeding program begun in 1943 at my commercial nursery in Hayward, Calif. It was invented by crossing undisseminated seedling 57 D-2 and pollen parent "Ripples", U.S. Plant Pat. No. 2,939 granted Sept. 16, 1969. The object of the cross was to produce a larger, faster-growing plant, with a better red color and very double flowers similar to the double flower form of the pollen parent "Ripples". It has been grown under normal greenhouse environmental conditions at Hayward, Calif., and annual asexual reproduction of my new variety by cuttings since 1974 show that the new and distinct characteristics of the hybrid come true to form and are established and transmitted through succeeding propagations.

DESCRIPTION OF THE PHOTOGRAPH

This new variety of azalea plant, "Super Red", is illustrated by the accompanying photographs which show the form and color characteristics of the plant and its bloom and foliage; the color rendition being as nearly true as is reasonably possible to obtain by conventional photographic procedures.

The upper photograph shows a close-up view of the flowers, and the lower photograph shows the entire plant.

DETAILED DESCRIPTION

Referring to the botanical details of this new variety, the following is an outline description. All plants were grown under normal environmental conditions in greenhouses and all color readings were taken in the greenhouse during day light hours. All colors are based on the Royal Horticultural Society Colour Chart.

I. Plant:

*Name.*—Super Red.

*Taxonomic status.*—Hybrid cultivar of Azalea plant, genus Rhododendron.

*Origin.*—Seed parent was an undisseminated seedling 57 D-2 and pollen parent was U.S. Plant Pat. No. 2,939 "Ripples".

*Growth.*—Very rapid growth, twice the rate of the pollen parent, forming a crown approximately 20 cm in diameter after 18 months. Height of the plant at 18 months is approximately 20 centimeters.

*Blooming habit.*—When grown outdoors in Hayward, Calif., it is normally at peak bloom about the first of March.

When "forced" grown in greenhouses (with a nighttime temperature of 60°) in the San Francisco Bay area during December for florists to sell at the Christmas season, they go from complete dormancy to colored bud stage in approximately 18 to 21 days.

When "forced" grown in greenhouses (with a nighttime temperature of 60°) in the San Francisco Bay area during January for florists to sell during the Valentines Day Holiday, the plant goes from complete dormancy to colored bud stage in approximately 15 to 18 days average.

II. Foliage:

*Size.*—Blade: 1.7–5.8 cm long × 1.1–3.8 cm broad. Petiole: 6–12 mm long × 1–2 mm broad.

*Shape.*—Broadly elliptic with a mucronate apex.

*Color.*—Upper leaf surface: deeper and greener than Parsley Green 00962 with a sheen. The hairs are brown.

*Margin.*—Ciliate, surface: strigose.

III. Flower:

*Inflorescence.*—In terminal clusters, 1–4 blooms per cluster. These with pedicels 8–12 mm long × 1–2 mm broad.

*Calyx.*—Pentamerous: the lobes broadly lanceolate, 5–6 mm × 3–4 mm. Color: about Pea Green 61/2. Texture: strigose, the hairs silvery, 1–2 mm long.

*Corolla.*—Size: large, 6–8 cm broad × 3–4 cm deep. Shape: very broadly funnel form, the outer whorl becoming rotate. Form: very double ruffled, by virtue of numerous (15–30) petaloids. Color: "Geranium Lake" 2-/1. Markings: faint venation, slightly darker than background, color about "Cherry" 722. Texture: adaxial surface: obscurely roughened, lustrous, opalescent.

IV. Reproductive organs:

*Androecium.*—Absent, or 1 or more rudimentary stamens present, these curved, 1–2 cm long, or anther-like organs occasionally to be found on an innermost petaloid, generally lacking pollen.

*Gynoecium.*—Absent.

I claim:

1. A new and distinct variety of Azalea plant as described and illustrated, known by the cultivar name "Super Red", and particularly characterized by the extra double, very large, clear red bloom on a vigorous, fast-growing plant with excellent foliage.

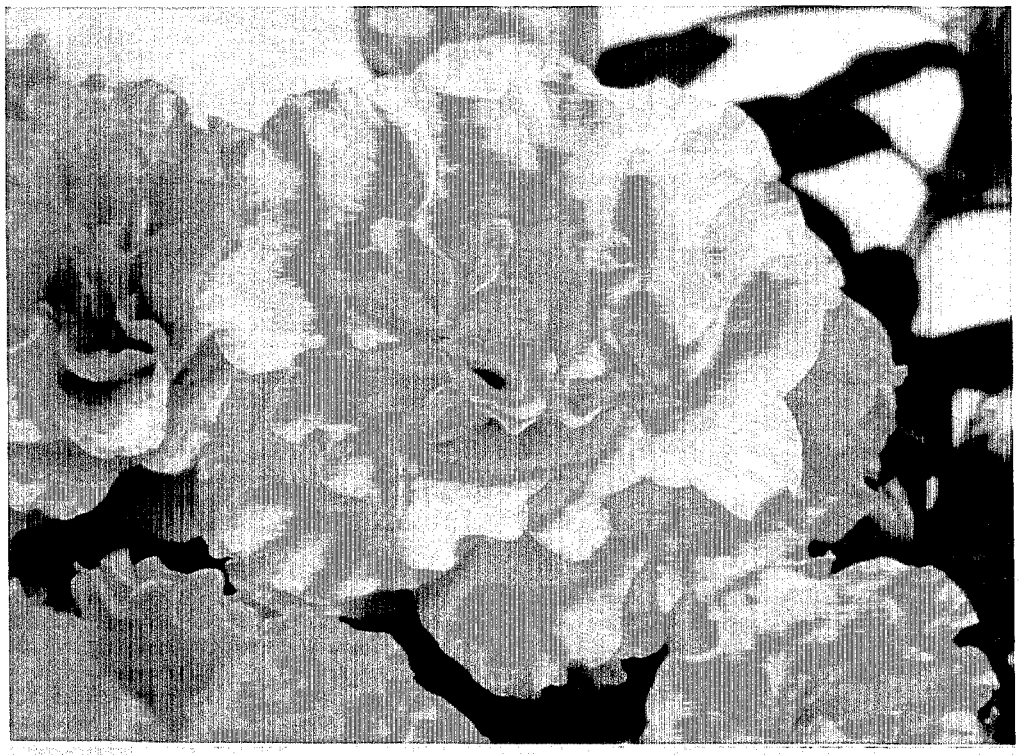
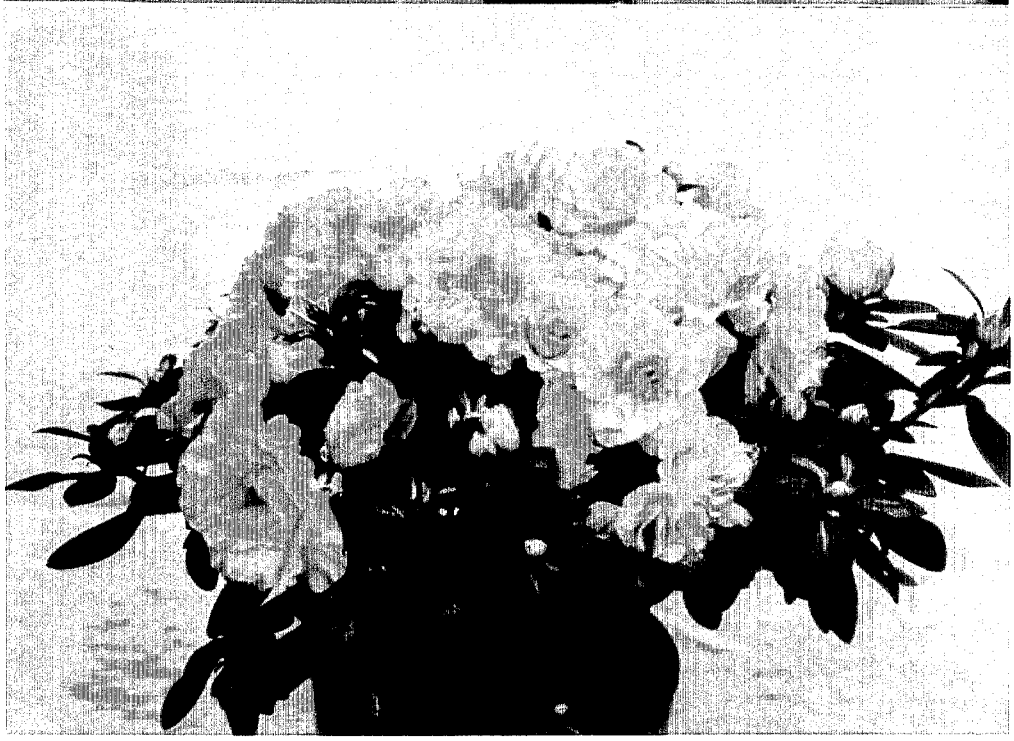

* * * * *